United States Patent

Schläpfer

[11] Patent Number: 5,584,832
[45] Date of Patent: Dec. 17, 1996

[54] HOOK WITH SCREW FOR TREATMENT OF VERTEBRAL COLUMN DEFORMITIES

[75] Inventor: Johannes F. Schläpfer, Glarus, Switzerland

[73] Assignee: Synthes (U.S.A.), Paoli, Pa.

[21] Appl. No.: 117,045

[22] PCT Filed: Mar. 15, 1993

[86] PCT No.: PCT/CH93/00070

§ 371 Date: May 9, 1994

§ 102(e) Date: May 9, 1994

[87] PCT Pub. No.: WO94/21186

PCT Pub. Date: Sep. 29, 1994

[51] Int. Cl.[6] ............................................. A61B 17/70
[52] U.S. Cl. ................................................ 606/61
[58] Field of Search ............................ 606/61, 72, 73

[56] References Cited

U.S. PATENT DOCUMENTS 5,000,165  3/1991  Watanabe .......................... 606/61
5,263,954  11/1993 Schlapfer et al. ................... 606/61

FOREIGN PATENT DOCUMENTS 0348272  12/1989  European Pat. Off. .
0517059  12/1992  European Pat. Off. .
2151475   4/1973  France .
2642642   8/1990  France .

OTHER PUBLICATIONS

J. Dubousset & Y. Cotrel, "Die CD–Instrumentation in der Behandlung von Wirbelsaulendeformitaten", Orthopade (1989) 18:118–127.

Primary Examiner—Tamara L. Graysay
Attorney, Agent, or Firm—Davis Hoxie Faithfull & Hapgood LLP

[57] ABSTRACT

This hook serves to treat vertebral column deformities. It is comprised of a shaft portion (2) with a longitudinal axis (1) to which a longitudinal support rod (5) can be attached transversely to the longitudinal axis (1), as well as a hook body (3) with a convex posterior side (34) and a concave anterior side (35) bent away from the longitudinal axis (1) connecting to the shaft portion (2). It is provided with a penetrating drill hole (36) extending from the convex posterior side (34) to the concave anterior side (35), to accept a screw (4).

11 Claims, 3 Drawing Sheets

5,584,832

HOOK WITH SCREW FOR TREATMENT OF VERTEBRAL COLUMN DEFORMITIES

This invention relates to a hook for correction of spinal deformities.

It is often necessary to treat thoracic vertebral column deformities surgically. The anatomy of the vertebral column must be restored and maintained. For this, fixation systems are used either dorsally or ventrally. Dorsal systems generally consist of at least one longitudinal support, but most have a left and a right support, and individual anchoring elements. The latter form a load-transferring connection between the vertebral column and the longitudinal support.

Currently there are three possibilities known for connecting the longitudinal support to the vertebral column: wire cerclages, pedicular screws and vertebral column hooks.

The wire cerclages are placed along the lamina and the spinous processes of the spinal vertebrae. There is a certain risk connected with the attachment of wire cerclages for the patient, since they may injure the spinal cord. In addition, the wires may, over time, cut through the bones (high local tension peaks cause resorption of the bones under the wire) or may simply break.

Pedicular screws are generally screwed through the pediculus into the vertebra. The pediculi are very narrow in the upper thoracic vertebral column and difficult to locate due to the deformity. The use of pedicular screws in this area therefore poses a high risk. In addition, many surgeons generally avoid using pedicular screws in the area of the thoracic vertebral column.

Vertebral column hooks are currently the elements most often used. Depending on the situation, they are placed on the lamina, the pediculus or the transverse process of the vertebrae. In contrast to the wire cerclages, they offer the advantage that the stress is transferred to a relatively large area of the bone and accordingly there is hardly any bone resorption at the point of contact between bone and hook. The hooks have, however, in contrast to the pedicular screws, the major disadvantage that they can transfer stress to the longitudinal support only when they are pressed firmly against the bone. With current systems such an initial load can be applied only through the longitudinal support. This makes it very difficult to manipulate the vertebrae in the area of the deformity with currently known hooks. The invention is intended to create remedial measures here. The invention is based on the task of creating a hook firmly and stably connected to the vertebra.

These difficulties are overcome or ameliorated by means of a hook comprising a shaft portion having a longitudinal axis, receiving means for seating a support rod positioned transversely to the axis and a curved hook body having a first end connected to said shaft portion, a second free end, and a curved section connecting said first and second ends forming a bight between the first end and the second end, and a hole in the curved section of the curved hook body adjacent the first end, the hole having a central longitudinal axis extending into the bight at an angle to the longitudinal axis.

Pedicular hooks pursuant to the invention are suitable, in particular, for thoracic application. Due to the additional screws insertable through the hook shaft, the pedicular hook can be pressed firmly into the osseous seat. The screw here is introduced from the caudal to the cranial (at an angle of approximately 120°–125° to the longitudinal axis of the pedicular hook) through the hook shaft into the main mass of the facet joint or to the corresponding vertebra. Thus, the pedicular hook can transfer forces and torque like a pedicular screw without slipping out from its osseous anchorage, which forms the precondition for the execution of a segmental correction.

There are many other advantages to the invention:

- Due to the independent, stable connection of the hook according to the invention with the vertebra, the hook can be manipulated individually;
- The vertebral column deformity to be treated can be corrected step by step from the less deformed side;
- The assembly of the hook is more sure in the thoracic range than the insertion of pedicular screws, since the hooks serve simultaneously as the drilling guides for the bone screws;
- The hook can be pressed optimally into the osseous site based on the sloped position of the bone screws.

The fastening of the hook pursuant to the invention to the longitudinal support, within a vertebral column fixation device, may be handled in many known ways. For this purpose, the shaft portion of the hook pursuant to the invention has corresponding design elements that permit connection to the longitudinal support, for example as disclosed in EP-A 0 348 272.

The clinical application of the hooks pursuant to the invention is analogous to those known systems and is described in detail in J. Debousset and Y. Cotrel, Orthopäde (1989) 18:118–127 "The CD-Instrumentation in der Behandlung von Wirbelsäulendeformitäten [CD Instruments in the Treatment of Vertebral Column Deformities].

Methods of embodiment of the invention that simultaneously explain the functional principle are shown in the drawings and described in greater detail below, where, in all drawings, a pedicular hook is shown as the method of embodiment.

Figure 1:
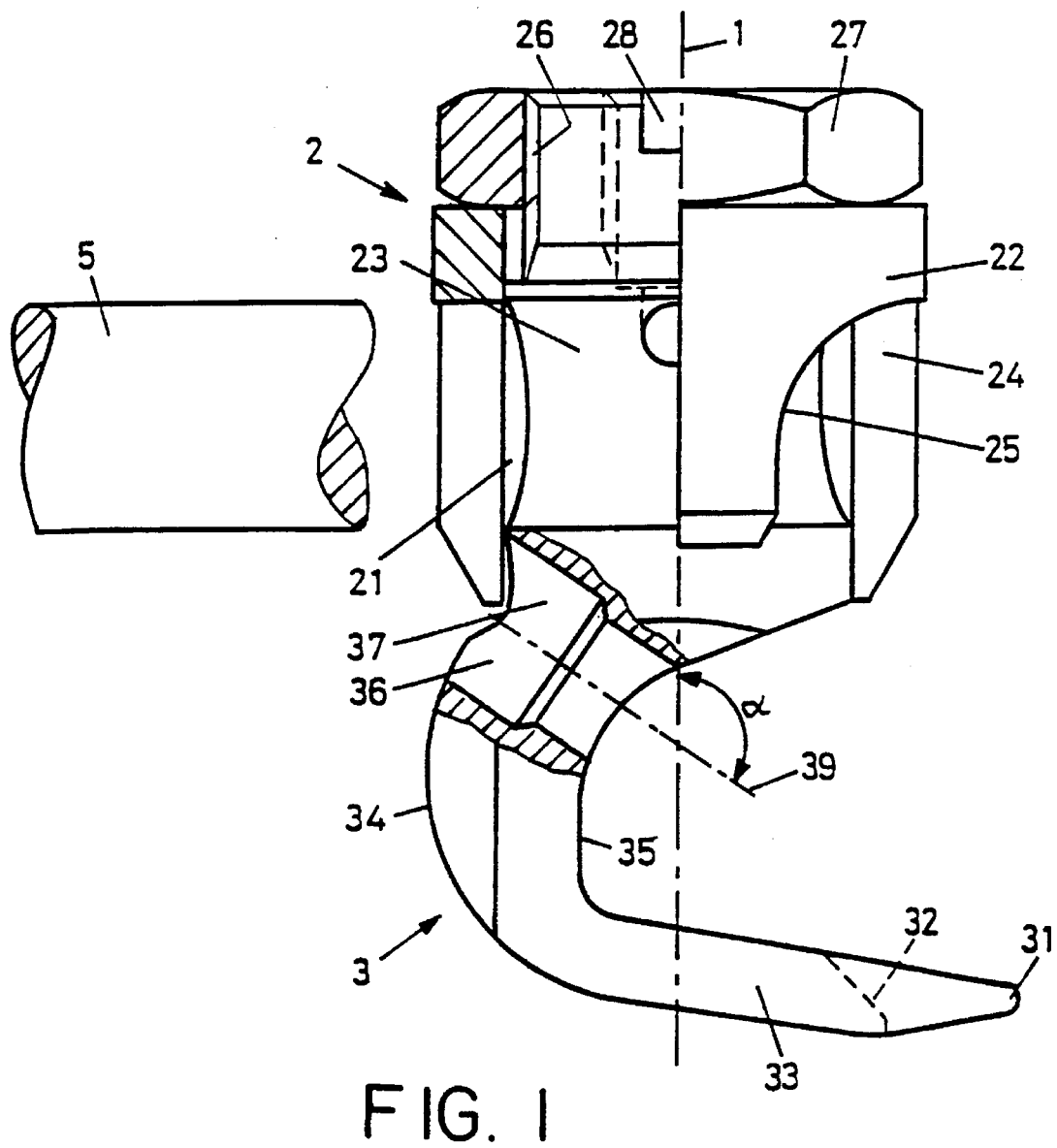
FIG. 1 shows a longitudinal view through the pedicular hook pursuant to the invention.

The pedicular hook shown in FIG. 1 in detail consists essentially of shaft portion 2 that can be fastened to longitudinal support rod 5 and a curved hook body 3 connected thereto. The curved hook body has a first end connected to the shaft portion, a second free end and a curved section forming a bight 35.

Shaft portion 2 consists of a connecting device that is described in greater detail in the patent application published under No. EP-A1 517 059.

It consists essentially of external element 22 with a circular cylindrical drill hole 21 and internal element 23 rotatable around axis 1 and displaceable in drill hole 21. Both elements 22 and 23 have two penetrating openings 24 and 25 jointly forming a channel transverse to axial direction 1 of the two elements 22 and 23 to accept longitudinal support rod 5. If longitudinal support 5 is introduced into the two drill holes 24 and 25, the axial displaceability of internal element 23 in drill hole 21 of external element 22 is blocked in one direction and its rotation is restricted to the angle range of through openings 24 and 25 of the two elements 22 and 23. Internal element 23 can be elastically deformed due to its through opening 25 in comparison to its axis 1, and, moreover, has external threading 26 which cooperates with nut 27. In case of axial tension on internal element 23 via nut 27, which causes an axial displacement of internal element 23 relative to external element 22, expansion of the elastically deformable internal element 23 occurs and tension on the same inside drill hole 21 of external element 22 with simultaneous blockage of the entire connection device and longitudinal support rod 5 inserted therein. Nut 27 is tightened or loosened via two instruments (not shown in the drawings), a socket wrench and a suitable instrument that holds the pedicular hook in place when manipulating nut 27. This instrument is introduced into longitudinal slot 28 of nut 27 like a screwdriver.

Through opening 25 is constructed with the advantage that longitudinal support 5 need not necessarily run parallel to hook body 3. This prevents the hook pursuant to the invention from being unnecessarily stressed with screw 4 during the assembly of longitudinal support rod 5, which conceals the danger that screw 4 may be torn from its anchoring in the bone. In the case of severe scolioses, a 100% correction is frequently impossible. In these cases, it is advantageous to have hooks with a through opening perpendicular (instead of parallel) to longitudinal support rod 5. To create this, drill hole 21 of shaft portion 2 is arranged at a right angle to hook body 3 instead of parallel to it, to accept a longitudinal support spacer (or transverse support) with an enlarged profile, that has a through opening to accept the actual longitudinal support. Via this longitudinal support rod spacer it is possible to connect longitudinal support 5 with the hook not only centrally but rather at a certain distance from longitudinal axis 1. The through opening in the longitudinal support spacer can be closed or open and can be constructed in such a manner that the longitudinal support spacer can be rotated a certain amount with reference to hook body 3. The advantage of this method of embodiment (not shown in the drawings) is grounded in the fact that by this means, unnecessary forces during assembly of the longitudinal support spacer can be avoided.

Instead of the above-described, preferred connecting device for shaft portion 2, any other known connecting system can be used to fix shaft portion 2 to longitudinal support 1, for instance, pursuant to EP-A1 348 272.

Hook body 3 is convex on its posterior side 34 and bifurcated at its free end 31. The two legs 33 form bay 32 adapted to pedicular geometry. The length of the two legs 33 can be different, as described in detail in the European Patent Application published under No. EP-A1 0 517 059. Bent-away free end 31 of hook shaft 2 runs essentially perpendicular to longitudinal axis 1.

At convex posterior side 34 of hook body 3, through drill hole 36 extending to curved section forming a bight 35 is provided to accept a screw 4. The longitudinal axis 39 of drill hole 36 preferably lies at an angel α of 115 to 130 degrees, preferably form 120 to 125 degrees to the longitudinal axis 1, and extends to said bight 35.

Figure 2:
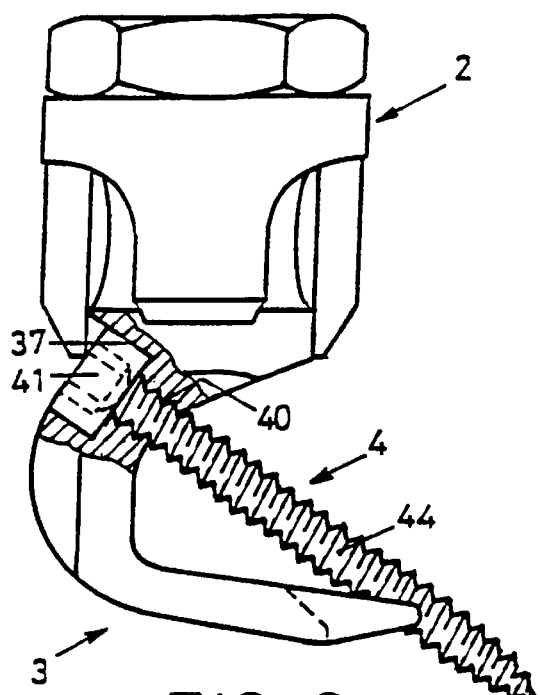
FIG. 2 shows a partial view through the pedicular hook pursuant to the invention with a screw inserted.
Figure 3:
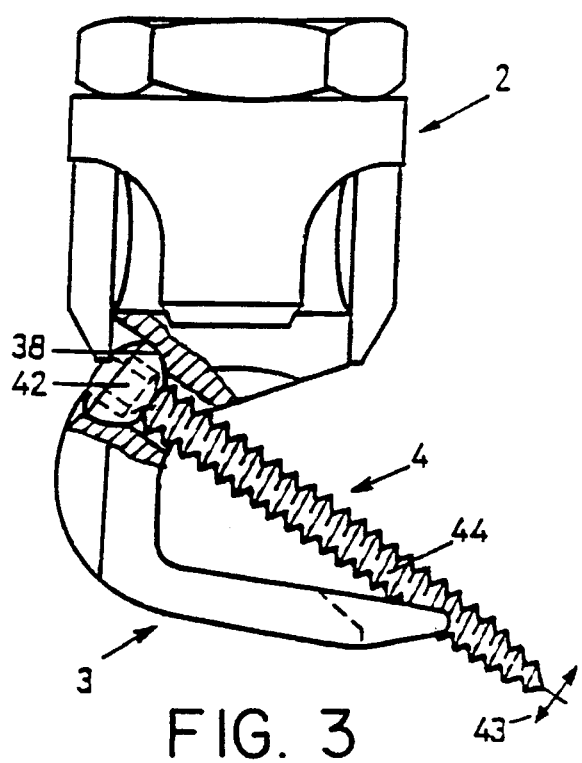
FIG. 3 shows a partial view through the pedicular hook pursuant to the invention with a modified screw.

As shown in FIG. 2, drill hole 36 can have cylindrical section 37 to accept screw 4 provided with cylindrical head 41. Instead, as shown in FIG. 3, drill hole 35 can also have spherical section 38 to accept screw 4 with spherical head 42. The method of embodiment with spherical section 38 permits, within certain limits, a spatial displaceability of screw 4, indicated by arrow 43; meanwhile, in the method of embodiment with cylindrical section 37, screw 4 is introduced.

Figure 2A:
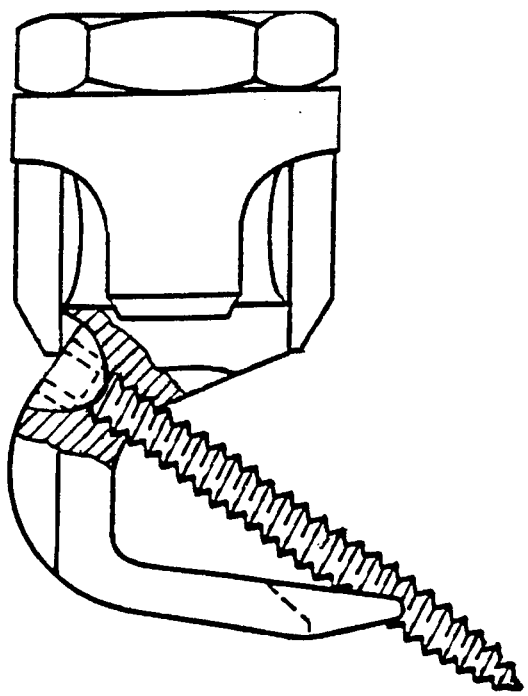
FIG. 2A shows a partial view through the pedicular hook pursuant to the invention with a modified screw.

Drill hole 36 can also be formed conically with a similar effect as with cylindrical screw 4, as shown in FIG. 2A.

Drill hole 36 can, as shown in FIG. 2, have a thread 40, which corresponds, at least in slope, to thread 44, of screw 4. In this case, it is possible to hold concave anterior side 35 of hook body 3 at a precisely defined distance from the bone. A further advantage of this method of embodiment consists in the fact that screw 4 is tensioned in the hook by tightening. This prevents screw 4 from unscrewing itself over time from the bone. In the other methods of embodiment, the unscrewing of screw 4 is impeded by the fact that the screw head (41, 42) is placed directly under longitudinal support rod 5.

Figure 4:
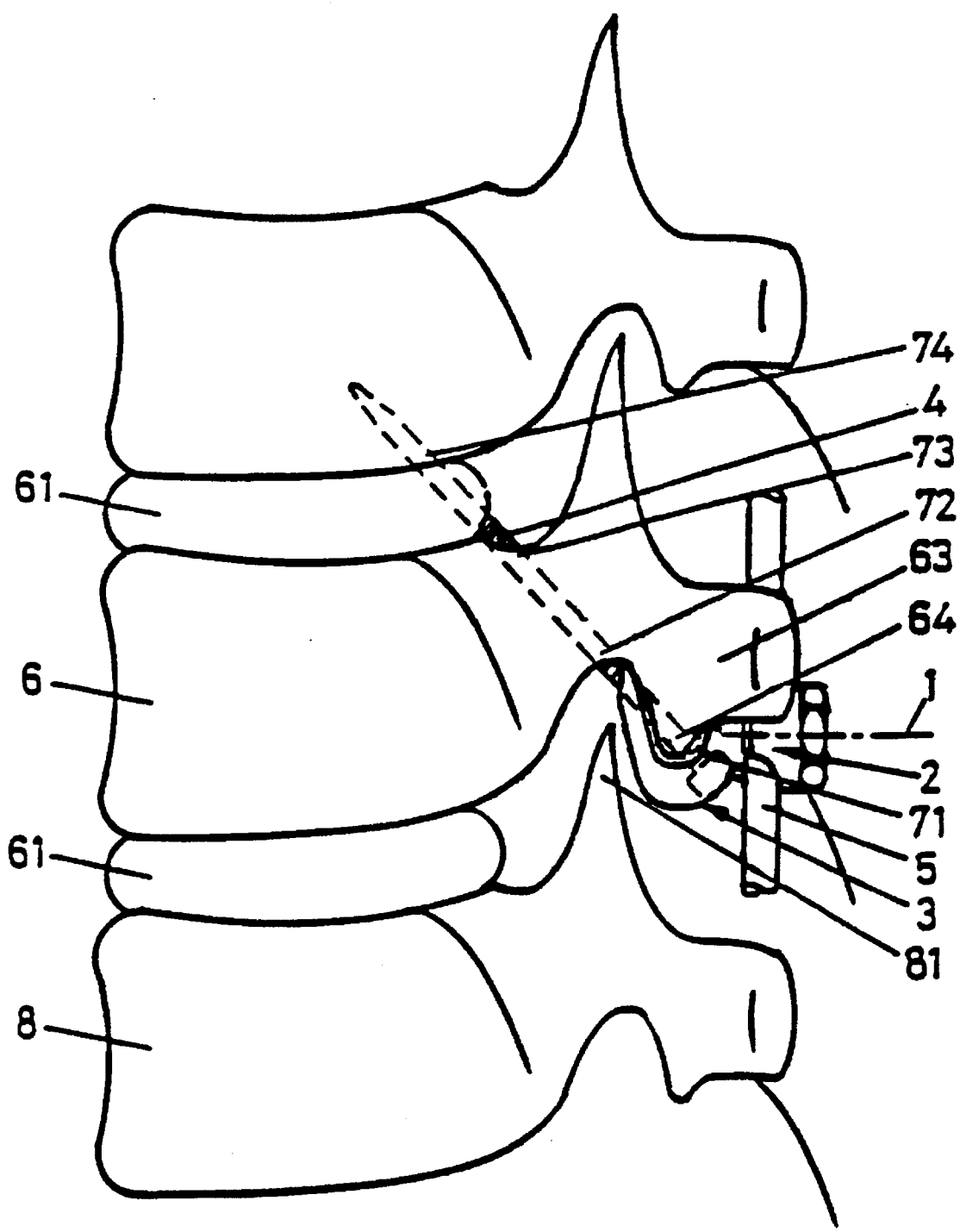
FIG. 4 shows a lateral view of the pedicular hook pursuant to the invention implanted in the vertebrae.

As shown in FIG. 4, the pedicular hook pursuant to the invention is inserted between lower facet joint 64 of vertebra 6 and upper facet joint 81 of vertebra 8 distanced by ligament disc 61 and lying under it, whereby hook body 3 from the caudal side embraces pediculus 63 due to its forked formation. Bone screw 4 is anchored in lower facet joint 64 of vertebra 6 and penetrates or contacts up to four cortical zones, depending on their length (71, 72, 73, 74).

Segmental correction in scoliosis is considered the main indication for the use of this method of embodiment. The goal of scoliosis treatment is to bring the vertebra toward the longitudinal support and to counter-rotate the twisted vertebra. In the devices pursuant to the state of the art, this occurs in such manner that the vertebral column is corrected in one single step, by rotating the longitudinal support from the anterior plane to the sagittal plane (so-called global correction). With this method of correction the counter-rotating torque applied to the vertebral column is very slight, since the caudal hook lying on the apex vertebra must be hooked into the lamina and thus lies practically over the rotational center.

It is claimed:

1. A hook for the treatment of vertebral column deformities comprising:

a shaft portion having a longitudinal axis, a channel in said shaft portion transverse to said longitudinal axis for seating a support rod;

a curved hook body having a first end connected to said shaft portion, a second free end, a curved section connecting said first and second ends forming a bight between said first end and said second end, and a hole in said curved section of said curved hook body adjacent said first end, said hole having a central longitudinal axis extending into said bight at an angle to said longitudinal axis.

2. The hook of claim 1, characterized in that the central axis of the hole includes an angle of 115 to 130 degrees to the longitudinal axis of the shaft portion.

3. The hook of claim 2, wherein the angle is from 120 to 125 degrees.

4. The hook of claim 1, characterized in that the hole has a cylindrical section adapted to accept a screw provided with a cylindrical head.

5. The hook of claim 1, characterized in that the hole has a spherical section adapted to accept a screw provided with a spherical head.

6. The hook of claim 1, characterized in that the hole has at least in part a threading adapted to received a threaded screw.

7. The hook of claim 1, characterized in that the second free end of the hook has a bent-away free end essentially perpendicular to the longitudinal axis of the shaft portion.

8. The hook of claim 1, characterized in that the hook is formed as a pedicular hook.

9. The hook of claim 1, characterized in that the shaft portion has a clamping device adapted to fix the support rod perpendicular to the longitudinal axis of the shaft.

10. The hook of claim 1, wherein the hole has a conical section adapted to accept a screw provided with a conical head.

11. The hook of claim 1, wherein the second free end of the hook is provided with a bay dividing the second free end into two legs.

\* \* \* \* \*

UNITED STATES PATENT AND TRADEMARK OFFICE
CERTIFICATE OF CORRECTION

PATENT NO. : 5,584,832
DATED : December 17, 1996
INVENTOR(S) : Johannes F. Schlapfer It is certified that error appears in the above-identified patent and that said Letters Patent is hereby corrected as shown below:

Col. 3, line 14, after "support" insert --rod--

Col. 3, line 29, after "support" insert --rod--.

Col. 3, line 53, "form" should be --from--.

Signed and Sealed this

Tenth Day of March, 1998

Attest:

BRUCE LEHMAN

Attesting Officer

Commissioner of Patents and Trademarks